US00PP32835P2

(12) United States Plant Patent
Trees

(10) Patent No.: US PP32,835 P2
(45) Date of Patent: Feb. 23, 2021

(54) ***VERBENA* PLANT NAMED 'BALENDREDIM'**

(50) Latin Name: ***Verbena* hybrid**
Varietal Denomination: Balendredim

(71) Applicant: Ball Horticultural Company, West Chicago, IL (US)

(72) Inventor: Scott C. Trees, Arroyo Grande, CA (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 16/884,243

(22) Filed: May 27, 2020

(51) Int. Cl.
*A01H 6/86* (2018.01)
*A01H 5/02* (2018.01)

(52) U.S. Cl.
USPC ..... Plt./308

(58) Field of Classification Search
USPC ..... Plt./308
See application file for complete search history.

*Primary Examiner* — Annette H Para
(74) *Attorney, Agent, or Firm* — Audrey Charles

(57) ABSTRACT

A new and distinct cultivar of *Verbena* plant named 'Balendredim', characterized by its bright red-colored flowers, dark green-colored foliage, and vigorous, mounded-spreading growth habit, is disclosed.

1 Drawing Sheet

Latin name of genus and species of plant claimed: *Verbena* hybrid.
Variety denomination: 'Balendredim'.

BACKGROUND OF THE INVENTION

The present invention relates to a new and distinct cultivar of *Verbena* plant botanically known as *Verbena* hybrid and hereinafter referred to by the cultivar name 'Balendredim'.

The new cultivar originated in a controlled breeding program in Arroyo Grande, Calif. during March 2015. The objective of the breeding program was the development of *Verbena* cultivars that are durable to environmental stresses, have dark green-colored foliage, and a mounded-spreading growth habit.

The new *Verbena* cultivar is the result of cross-pollination. The female (seed) parent of the new cultivar is the proprietary *Verbena* hybrid breeding selection coded 18664, not patented, characterized by its dark red-colored flowers, medium green-colored foliage, and moderately vigorous, mounded growth habit. The male (pollen) parent of the new cultivar is the proprietary *Verbena* hybrid breeding selection coded 18205, not patented, characterized by its dark red-colored flowers, dark green-colored foliage, and vigorous, spreading growth habit. The new cultivar was selected as a single flowering plant within the progeny of the above stated cross-pollination during April 2016 in a controlled environment in Arroyo Grande, Calif.

Asexual reproduction of the new cultivar by terminal stern cuttings since April 2016 in Arroyo Grande, Calif., and West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balendredim' as a new and distinct cultivar of *Verbena* plant:

1. Bright red-colored flowers;
2. Dark green-colored foliage; and
3. Vigorous, mounded-spreading growth habit.

Plants of the new cultivar differ from plants of the female and male parents primarily by having a larger diameter inflorescence and a more spreading growth habit. Plants of the new cultivar differ from plants of the female and male parents primarily by having a larger diameter inflorescence and a more mounded growth habit.

Of the many commercially available *Verbena* cultivars, the most similar in comparison to the new cultivar is Endurascape Red 'Balendred', U.S. Plant Pat. No. 26,132. However, in side-by-side comparisons, plants of the new cultivar differ from plants of 'Balendred' in at least the following characteristics:

1. Plants of the new cultivar have more inflorescences per plant plants of 'Balendred';
2. Plants of the new cultivar have a slightly darker red-colored flower than plants of 'Balcadavlu'; and
3. Plants of the new cultivar have a wider habit than plants of 'Balendred'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs may differ slightly from the color values cited in the detailed description, which accurately describes the colors of 'Balendredim'. The approximately 6-month-old plants were grown in 4.5-inch pots for approximately 16 weeks and then 6-inch pots for approximately 5 weeks in a greenhouse in West Chicago, Ill. Plants were given one pinch two weeks after transplant.

DETAILED BOTANICAL DESCRIPTION

Figure 1:
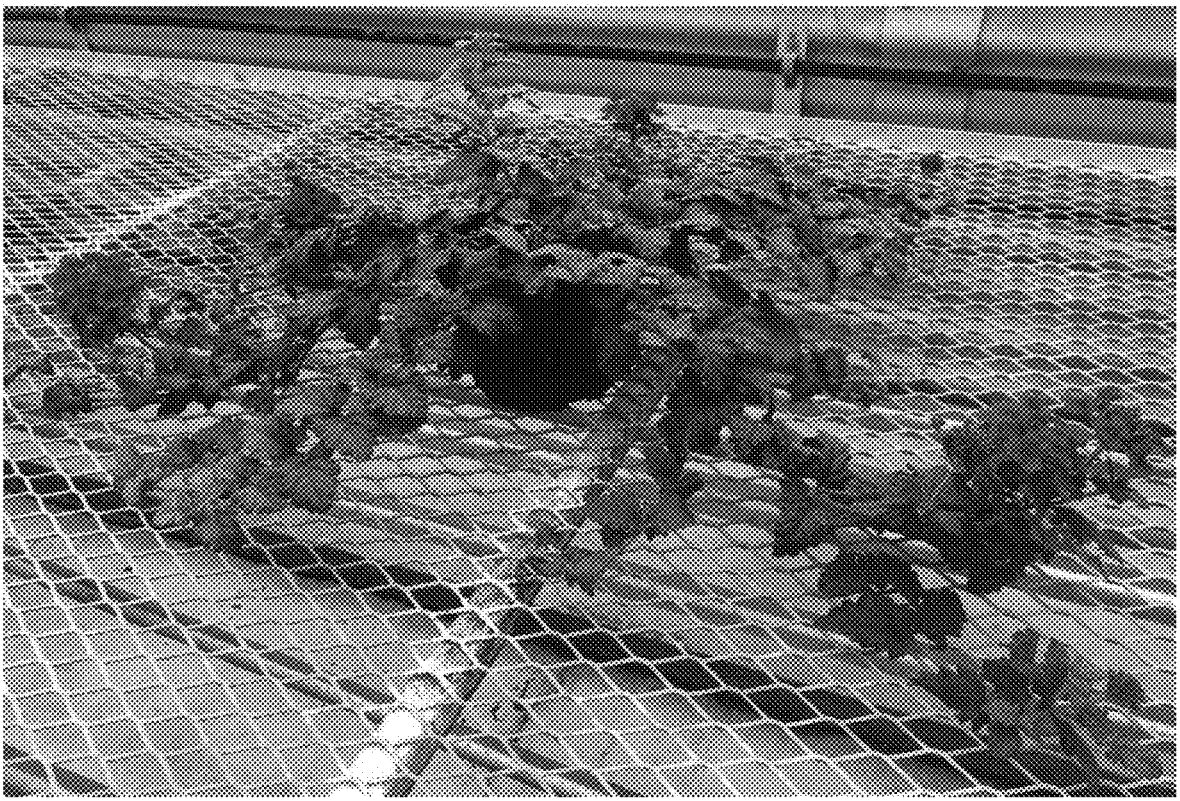
FIG. 1 illustrates a side view of the overall growth and flowering habit of 'Balendredim'.
Figure 2:
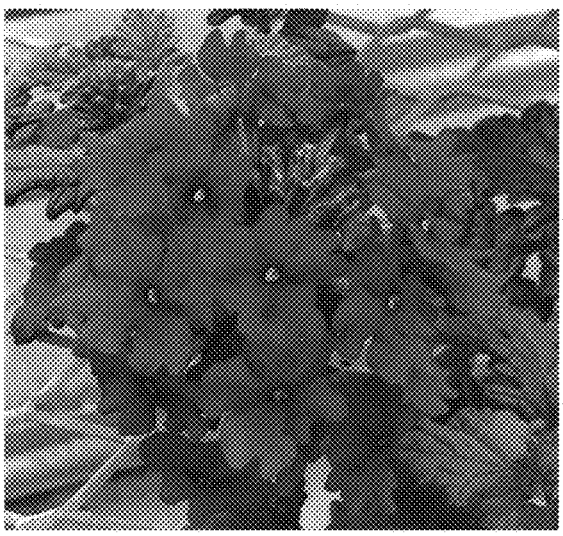
FIG. 2 illustrates a close-up view of an individual inflorescence of 'Balendredim'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in March 2020 under natural light conditions in West Chicago, Ill.

The following descriptions and measurements describe approximately 6-month-old plants produced from cuttings from stock plants and grown in a glass-covered greenhouse in West Chicago, Ill. under conditions comparable to those used in commercial practice. The plants were grown utilizing a soilless growth medium in 4.5-inch pots for approximately 16 weeks and then 6-inch pots for approximately 5 weeks. Plants were given one pinch two weeks after transplant, Greenhouse temperatures were maintained at approximately 67° F. to 72° F. (19° C. to 22° C.) during the day and approximately 65° F. to 68° F. (18° C. to 20° C.) during the night. Supplemental lighting was used. Measurements and numerical values represent averages of typical plants.

Botanical classification: *Verbena* hybrid 'Balendredim'.

Parentage:

*Female parent*.—Proprietary *Verbena* hybrid breeding selection coded 18664, not patented.

*Male parent*.—Proprietary *Verbena* hybrid breeding selection coded 18205, not patented.

Propagation:

*Type cutting*.—Terminal stem.

*Time to initiate roots*.—Approximately 6 to 9 days.

*Time to produce a rooted cutting*.—Approximately 24 to 28 days.

*Root description*.—Fibrous.

*Rooting habit*.—Freely branching.

Plant description:

*Commercial crop time*.—Approximately 5 to 7 weeks from a rooted cutting to finish in a 10 cm pot.

*Growth habit and general appearance*.—Vigorous, mounded-spreading.

*Size*.—Height from soil level to top of plant plane: Approximately 13.0 cm. Width: Approximately 76.0 cm.

*Branching habit*.—Freely branching, pinching enhances basal branching. Quantity of main branches per plant: Approximately 6.

*Branch*.—Shape: Square in cross section. Strength: Strong. Length: Approximately 38.0 cm. Diameter: Approximately 3.0 mm. Length of central internode: Approximately 4.0 cm. Texture: Densely pubescent with a mixture of glandular and nonglandular hairs. Gland color: Mixture of N92C and colorless, transparent. Color of young stems: 144A. Color of mature stems: 137B.

Foliage description:

*General description*.—Quantity of leaves per main branch: Approximately 20. Fragrance: None detected. Form: Simple. Arrangement: Opposite.

*Leaves*.—Aspect: Perpendicular to stem, obtuse angle with age. Shape: Ovate to oblong. Margin: Crenate. Apex: Broadly acute. Base: Truncate. Venation pattern: Pinnate. Length of mature leaf: Approximately 5.5 cm. Width of mature leaf: Approximately 4.0 cm. Texture of upper surface: Moderately pubescent. Texture of lower surface: Densely pubescent with a mixture of glandular and nonglandular hairs. Gland color: Colorless, transparent. Color of upper surface of young and mature foliage: Closest to but darker than NN137A with venation of 147C. Color of lower surface of young and mature foliage: Closest to 137B with venation of 147C.

*Petiole*.—Length: Approximately 6.0 mm. Diameter: Approximately 2.0 mm. Texture: Densely pubescent with a mixture of glandular and nonglandular hairs. Gland color: Colorless, transparent. Color: 147C.

Flowering description:

*Flowering habit*.—'Balendredim' is freely flowering under outdoor growing conditions with substantially continuous blooming from spring through autumn and year-round in greenhouse environment.

*Lastingness of individual flower on the plant*.—Approximately 5 to 7 days.

Inflorescence description:

*General description*.—Type: Corymb. Shape: Hemispherical. Quantity per plant: Approximately 5. Fragrance: None detected. Length or height: 5.0 cm. Width: Approximately 6.0 cm. Quantity of fully open flowers per inflorescence: Approximately 24.

*Peduncle*.—Strength: Strong. Aspect: Erect. Length: Approximately 7.0 cm. Diameter: Approximately 3.0 mm. Texture: Densely pubescent with a mixture of glandular and nonglandular hairs. Gland color: Mixture of N92C and colorless, transparent. Color: 137B.

Flower description:

*General description*.—Type: Sessile, salverform.

*Bud*.—Rate of opening: Generally takes 2 to 3 days for bud to progress from first color to fully open flower. Quantity of unopened inflorescences per plant: Approximately 7.

*Bud just before opening*.—Shape: Elongated, globular at apex. Length: Approximately 1.3 cm. Diameter: Approximately 3.0 mm. Petal portion 53A, sepal portion 137B.

*Corolla*.—Shape: Round. Diameter: Approximately 2.1 cm. Depth: Approximately 2.8 cm.

*Petals*.—Quantity: 5, fused at base forming a tube. Shape: Obovate. Appearance: Matte. Margin: Entire. Apex: Emarginate. Length of upper petals from tube: Approximately 9.0 mm. Width of upper petals: Approximately 8.0 mm. Length of lateral petals from tube: Approximately 1.0 cm. Width of lateral petals: Approximately 1.0 cm. Length of lower petal from tube: Approximately 1.0 cm. Width of lower petal: Approximately 1.1 cm. Texture of upper surface: Glabrous with glandular pubescent base. Texture of lower surface: Sparsely pubescent with a mixture of glandular and nonglandular hairs. Gland color: Mixture of N92C and colorless, transparent. Color of upper surface when first open: 46A with N187A at throat opening. Color of lower surface when first and fully open: 47C with NN155D at base. Color of upper surface when fully open: 45A with 187A at throat opening. Color of whiskers surrounding the opening of the corolla tube: N81C.

*Corolla tube*.—Length: Approximately 2.0 cm. Diameter at proximal end: Approximately 1.0 mm. Diameter at distal end: Approximately 2.0 mm. Texture of outer surface: Upper half moderately pubescent, lower half glabrous. Texture of inner surface: Upper half densely pubescent, lower half moderately pubescent. Color of outer surface: 145D to 145C with an overlay of N79B at distal end. Color of inner surface: 145D to 145C with an underlay of N79B at throat opening.

*Calyx*.—Shape: Tubular with 5 acute tips. Length: Approximately 1.2 cm. Width: Approximately 3.0 mm.

*Sepals*.—Quantity per flower: 5, fused at base. Shape: Linear. Apex: Acute. Length: Approximately 1.2 cm. Width: Approximately 1.0 mm. Texture of inner surface: Moderately pubescent. Texture of outer surface: Densely pubescent with a mixture of glandular and nonglandular hairs. Gland color: Mixture of N92C and colorless, transparent. Color of inner and outer surfaces: 137B.

*Stipules*.—Shape: Lanceolate. Apex: Acute. Length: Approximately 6.0 mm. Width at base: Approximately 2.0 mm. Texture of inner surface: Glabrous. Texture of outer surface: Densely pubescent with a mixture of glandular and nonglandular hairs. Gland color: Mixture of N92C and colorless, transparent. Color of inner and outer surfaces: 144A at base transitioning to 137A at apex.

*Reproductive organs*.—Androecium: Stamen quantity: 4, didynamous. Stamen length of longer pair: Approximately 2.0 mm. Stamen length of shorter pair: Approximately 1.0 mm. Anther shape: Bilobed, ovoid. Anther length: Approximately 1.0 mm. Anther color: N144D. Pollen amount: Moderate. Pollen color: 1D. Gynoecium: Pistil quantity: 1 per flower. Pistil length: Approximately 2.0 cm. Stigma shape: Bifid. Stigma length: Less than 1.0 mm. Stigma color: 137A. Style length: Approximately 1.9 cm. Style color: 145D with 145B tinted with 187A near stigma. Ovary diameter: Approximately 1.0 mm. Ovary texture: Glabrous. Ovary color: 144A.

Seed and fruit production: Neither seed nor fruit production has been observed.

Disease and pest resistance: Resistance to pathogens and pests common to *Verbena* has not been observed.

What is claimed is:

1. A new and distinct cultivar of *Verbena* plant named 'Balendredim', substantially as herein illustrated and described.

* * * * *